United States Patent
Kleinhenz et al.

(10) Patent No.: US 7,316,657 B2
(45) Date of Patent: Jan. 8, 2008

(54) MASSAGE APPLIANCE WITH ADJUSTABLE MASSAGE CHARACTERISTICS AND STORAGE CONTAINER

(75) Inventors: Sven Kleinhenz, Rellingen (DE); Bernhard Felten, Pinneberg (DE)

(73) Assignee: Beiersdorf AG, Hamburg (DE)

( * ) Notice: Subject to any disclaimer, the term of this patent is extended or adjusted under 35 U.S.C. 154(b) by 184 days.

(21) Appl. No.: 10/917,586

(22) Filed: Aug. 13, 2004

(65) Prior Publication Data
US 2005/0059914 A1    Mar. 17, 2005

Related U.S. Application Data

(63) Continuation of application No. PCT/EP03/01350, filed on Feb. 12, 2003.

(30) Foreign Application Priority Data
Feb. 15, 2002 (DE) ............................... 102 06 257

(51) Int. Cl.
*A61H 7/00* (2006.01)
(52) U.S. Cl. .................. 601/17; 601/135; 601/137; 601/154
(58) Field of Classification Search .................. 601/17, 601/15, 114, 135, 137, 138, 154; 401/272, 401/273
See application file for complete search history.

(56) References Cited

U.S. PATENT DOCUMENTS

| 2,584,735 | A |   | 2/1952  | Pancoast |
|-----------|---|---|---------|----------|
| 3,994,290 | A | * | 11/1976 | Springer et al. ............ 601/131 |
| 5,125,423 | A |   | 6/1992  | Butterbrodt |
| 5,181,504 | A | * | 1/1993  | Ono et al. ..................... 601/70 |
| 5,647,841 | A | * | 7/1997  | Groenewold et al. ........ 601/114 |
| 5,725,483 | A | * | 3/1998  | Podolsky ...................... 601/15 |
| 5,740,948 | A |   | 4/1998  | Chu et al. |
| 5,888,984 | A |   | 3/1999  | Brown |
| 6,054,547 | A | * | 4/2000  | Perry et al. .................... 528/15 |
| 2004/0151793 | A1 | * | 8/2004 | Paspaleeva-kuhn et al. ........................... 424/754 |
| 2004/0253197 | A1 | * | 12/2004 | Sakuta .................... 424/70.12 |
| 2004/0267170 | A1 | * | 12/2004 | Liste et al. .................. 601/17 |

FOREIGN PATENT DOCUMENTS

| DE | 199 46 192 A1 | 6/2001 |
| EP | 1 153 592 A1 | 11/2001 |
| GB | 643 633 A | 9/1950 |
| JP | 2001225859 | 8/2001 |
| WO | WO 00/48559 | 8/2000 |

* cited by examiner

*Primary Examiner*—Danton DeMille
(74) *Attorney, Agent, or Firm*—Greenblum & Bernstein, P.L.C.

(57) ABSTRACT

The present invention is a massage appliance comprising a preparation, a storage container containing the preparation, and a closure for the storage container. The closure comprises a massage device comprising an outlet opening through which the preparation can be applied to the surface to be massaged and an adjustment device comprising a first element with at least one first surface wherein the first surface contacts the surface to be massaged during a massage, and a second element arranged to be moveable relative to the first element. The adjustment device may be used to adjust a massage characteristic value of the first surface. The massage device is positioned at an angle with respect to the main axis of the storage container. The present invention also includes a method of applying a preparation to the skin, a method of treating rheumatoid arthritis, and a method of warming up using the massage appliance.

33 Claims, 2 Drawing Sheets

MASSAGE APPLIANCE WITH ADJUSTABLE MASSAGE CHARACTERISTICS AND STORAGE CONTAINER

CROSS-REFERENCE TO RELATED APPLICATIONS

This is a continuation application of PCT/EP03/01350, filed Feb. 12, 2003, which published as WO03/068128 on Aug. 21, 2003 and is incorporated herein by reference in its entirety, and also claims the benefit of German Priority Application No. 102 06 257.9, filed Feb. 15, 2002.

FIELD OF THE INVENTION

The present invention relates to a massage appliance consisting of a massage preparation, a container containing the massage preparation, and a massage device which is designed as a closure of the storage container and through an opening of which the preparation can be applied to the surface to be massaged. The massage device comprises two components via which a desired massage characteristic value, such as hardness or elasticity, of the massaging surface of the massage device can be adjusted. The massage appliance is suitable for use in the treatment of rheumatoid diseases.

BACKGROUND OF THE INVENTION

Containers, for example bottles or jars, are known which are used, among other things, to store liquids in the field of cosmetics, medicine and dermatology. The bottles are in most cases made of a flexible plastic, so that gentle pressure on the body of the bottle is sufficient to expel the liquid in the bottle out of the opening. Examples which may be mentioned here are the known plastic bottles for shower formulations, liquid soaps, shampoo, and massage oils. Bottles which can be closed with a screw-on cap are preferred. Tubes are suitable as containers for ointments, gels or pastes.

The containers are often produced by the extrusion blow-molding process.

U.S. Pat. No. 3,892,829 discloses a process and a device for the production of flat bottles from an extruded parison which is preblown in an intermediate mold and only then is transferred into a final blow mold, the mold cavity of which has the contour of the flat bottle that is to be produced.

DE 37 02 844 A1 discloses a process which follows this principle and an extrusion blow-molding machine which operates thereby. In this, a plastic parison is freely extruded, taken to an intermediate mold and blow-molded there to form a rotationally symmetrical intermediate molding. This intermediate molding, which consequently has a circular cross section at each height, already has approximately the length (height) of the flat bottle to be produced, and has in its main sections (base, body, neck) a circumference which is more or less approximate to the corresponding circumferences of the flat bottle. The latter is shaped by transferring the intermediate molding into a final blow mold, as is known from DE 27 20 448 C2, for example.

This technique, which is largely waste-free and accordingly free from pinch-off welds, for production of flat bottles of substantially uniform wall thickness has proven valuable.

In EP 0 688 658 A1, the intermediate molding is supported mechanically from underneath, at least during transfer from the intermediate mold into the final blow mold. The intermediate molding is supported by an additional movable mold part at least during transfer from the intermediate mold into the final blow mold. This mold part can advantageously match the base contour of the intermediate molding. As a rule, the mold part must be displaceable in the vertical direction, so that closing of the final blow mold is not impeded.

Massage devices have also been known for a long time. They exist in the most diverse of shapes and materials. They can be made of plastics or of naturally occurring materials.

Thus, a massage device is known which can be controlled electrically and is integrated into seating furniture, such as an armchair or the like. In this known massage device, one or more massage heads are arranged under the seat cover. These massage heads are driven electrically by electric motors, so that they are set in motion and a person sitting on the chair can be massaged at an appropriate place by means of the massage head.

A massage device is also known in which massage pins, distributed across the surface of a ball of plastic, extend in the radial direction from the ball surface, so that, for massage purposes, this ball can be rolled across the surface to be massaged or over the human body.

Massage applicators made of plastic can have the most diverse of shapes. Roller applicators/ball applicators and pin applicators are known.

In roller applicators or ball applicators, movable balls are held in a suitable guide, and a pure pressure massage is achieved in this way. The pressure massage is very skin-friendly, since the frictional resistance is reduced to a minimum.

Pin applicators made of rubber or soft plastic exhibit increased friction. This increased friction intensifies the massage effect in the upper layers of the skin, but can also lead to skin irritation on sensitive areas of skin. Generally speaking, a more intense massage effect is achieved by massage with a pin applicator. At the same time, massage with a pin applicator also leads to greater mechanical stressing of the skin and of the underlying tissue and therefore to an increased blood flow in the skin. The increased blood flow and the massage of the subcutaneous tissue leads to a strengthening of the subcutaneous tissue. This strengthening leads to an improvement in the appearance of the skin and thus prevents or counteracts cellulite.

The points mentioned in respect of massage applicators made of plastic also apply in general to massage applicators made of naturally occurring materials, for example wood. However, in the case of these applicators made of naturally occurring substances, there are also special forms which are made, for example, of braided sisal rope or similar materials. In these applicators, the rough surface of the naturally occurring substances is used for the massage.

The human body does not reach its full stature until about 20 years of age. Within this period, the still sensitive muscle and bone apparatus may become damaged. Areas of weakness can develop which, in the course of adult life, may lead to disease. Rheumatoid diseases are considered as being the number one disorder in this respect.

The term "rheumatoid diseases" covers painful disorders of the joints, muscles, nerves or tendons. These are caused by, among other things, external factors, such as cold or heat, or by overexertion. There are over 500 different known causes of pain of the muscles, joints and nerves. Known signs and symptoms include muscle tension, shoulder/arm pain, connective tissue pain after overexertion (muscle soreness), joint pain and nerve pain of the rheumatoid type; sports injuries (contusion, overstretching, compression), knee arthrosis, stiff neck (tension in the neck), back pain, sciatica and lumbago, peripheral circulation disorders, and nocturnal calf pain.

Possible triggers of all these states of pain may be
sitting the wrong way,
lack of movement,
incorrect posture when sitting, standing and lying,
lifting and carrying heavy weights in the wrong way,
overexertion,
cold and drafts.

In the case of muscle tension, the muscle tissue has poor blood flow and is not adequately supplied with oxygen and nutrients. Metabolic end products are not carried away and are able to accumulate. The painful muscle is automatically given protection and therefore has even less blood flowing through it—forming a vicious circle—and the pain intensifies. Relief is obtained only when pain conduction is blocked.

To eliminate the muscle tension, it is recommended to stimulate as much as possible the flow of blood through the affected parts of the body. The possible known ways of doing this include, in particular, massage, medical baths, specific sports activity, and gymnastics.

Special ointments accelerate, strengthen and prolong the tonicity-enhancing action, and the recovery time is thus reduced by earlier starting of body movement exercises.

Various massage products are also available as starting aids (vascular training) for physical exercises in sports/winter sports. These improve the working conditions of the muscles and thus help prevent muscle injury.

In the case of muscle pain and joint pain, heat plays an important role. In acute pain, relief can be obtained in particular from special, deep-acting creams, for example containing the active substances capsaicin and/or nicotinic acid derivatives.

N-Vanillyl nonanamide (nonivamide) is a synthetic capsaicin. The natural basis of capsaicin is paprika (Spanish pepper).

Capsaicin: N-(4-hydroxy-3-methoxybenzyl)-8-methylnon-trans-6-enamide

Starting materials of capsaicin-containing preparations are *Capsici fructus* (paprika). and *Capsici fructus acer* (cayenne pepper). The dried fruits of various *Capsicum* species are used, or the dried, mature fruits of *Capsicum frutescens*, in most cases freed of the calyx.

Constituents of cayenne pepper are the pungent substances of the vanillyl amide type, the capsainoids, with up to 77% capsaicin.

Nicotinic acid derivatives acted as intensifiers of capsaicin. Nicotinic acid is an important natural building block of skin and cell walls. One derivative of nicotinic acid is 2-butoxyethyl nicotinate (nicoboxil). Addition of nicoboxil can provide a 40% increase in the effect of capsaicin.

The active substance nonivamide acts by blocking nerve reflexes which conduct pain impulses. Nicoboxil promotes blood flow, so that the healing process in the affected tissue is assisted. The strong healing action of the heat lasts for several hours. Tension and cramps subside, pain is relieved, and mobility restored.

A commercial product containing a combination of the abovementioned active substances is Finalgon®. Finalgon is a product from the Thomae company and has been on the market since Feb. 15, 1951. Other products on the market contain, in addition to N-vanillyl nonanamide, benzyl nicotinate and diethyl salicylate (abc-Salbe® from Beiersdorf). In particular, N-vanillyl nonanamide directly stimulates the highly sensitive nerve endings in the skin and thus increases blood flow in the skin by up to 5 times and provides an up to 160% increase in blood flow in the muscles. With its especially prolonged duration of action, it alleviates tension rapidly and reliably and thus provides lasting pain relief. This mechanism of action is explained as follows:

When pain occurs, the cells in which pain perception starts are blocked (analgesic action). When a stimulus occurs, certain mediators are released which excite so-called receptors. These pick up the information and conduct the pain via the nerve fibers and through the spinal cord to the central nervous system in the brain (CNS). N-Vanillyl nonanamide intervenes directly in this and interrupts the pain conduction. This is because N-vanillyl nonanamide binds to certain receptors and thus suppresses conduction of the stimulus. 2-Butoxyethyl nicotinate supports and intensifies the action of N-vanillyl nonanamide.

In addition to the effect on the pain receptors, widening of the blood vessels also takes place. The flow of blood in the skin is increased. This is sensed by the user as a very intense sensation of heat ("burning"). The skin changes to a strong red color in places, and heating of the skin by up to 2 degrees can be detected. This reaction is sensed by many users as a sometimes unpleasant side effect, although it is completely harmless and does not damage the skin.

The effect of increased blood flow and heating of the skin means that the deeper-lying muscle tissue is also heated (promoting blood circulation). The muscles thus relax.

For an area the size of the palm of one's hand, only a pea-sized amount is needed, and this is usually massaged into the skin using the fingers and hands. Particularly for injured persons, every movement is often very painful, so that large areas of the surface of the body cannot easily be reached by the hands, let alone massaged. In this connection, the upper area of the back in particular causes problems when applying the substance without assistance.

BRIEF SUMMARY OF THE INVENTION

It is an object of the invention to make it easier for massage preparations to be applied and in particular also massaged in, even in areas of the body which are difficult to get at.

When using and applying massage preparations, the product often also wets and penetrates into the skin of the fingers and hands. It is often not possible to completely remove the residues of ointment by simply washing with normal hand-cleaning products. A sensation of heat which lasts for a period of hours up to days can then be felt in those areas of the skin of the hands and fingers that have been penetrated by the substance. If, at a later stage, sometimes up to several hours later, hands contaminated in this way touch sensitive areas of the skin, such as the mucous membranes or eyes, this causes severe irritation which, in the eye area, can also lead to permanent damage.

Avoiding these disadvantages by using gloves when massaging is something which many feel very unpleasant and is therefore not commonly done.

It is therefore an object of the present invention to simplify the application and massaging of massage preparations into the skin, without the products coming directly into contact with the hands.

It is surprising, and could not be predicted by the skilled person, that a massage appliance according to the main claim avoids the disadvantages of the prior art. The invention covers the combination of a massage preparation, contained in a storage vessel, with a massage device, so as to permit substantially improved use of the above-described massaging and heating products.

The massage appliance comprises a massage preparation, a storage container containing the preparation, and a massage device, also referred to as massage head. The massage device is designed as a closure of the storage container and is positioned at an angle to the main axis of the storage container. The device has an opening through which the preparation can be applied to the surface to be massaged. The massage device also comprises an adjustment device consisting of a first component, or first element, with at least one first surface which, during massage, is in contact with the surface to be massaged, and of a second component, or second element. A massage characteristic value can be adjusted in the area of the first surface using this adjustment device.

By virtue of the special design of the device, with the massage head arranged at an angle to the storage container, i.e. angled relative to the main axis of the product container, it is possible to massage areas of the back that are difficult to reach with one's own hands. The product container thus serves as an extension grip for the massage head.

The outlet opening for the massage product is designed in such a way as to prevent the preparation from flowing back and to prevent penetration of foreign substances. The configuration of the outlet opening with a self-closing check valve is therefore seen as an advantage.

Product containers according to the invention include flexible, hollow blow-molded articles made of plastic, tubes or rigid bottles. Bottles with a cylindrical design that can be gripped are particularly preferred. Very particular preference is given to containers with an ergonomic design, in which twisting in the hand during massage is prevented.

In a particular embodiment, the preparation is conveyed from the product container to the outlet opening on the massage head via an ascending tube, thus permitting application to the massage head in an upright position.

According to the invention, a massage device is proposed which has a first surface which, during massage, is in contact with the surface to be massaged. The massage device according to the invention is in particular configured in such a way that it comprises a massage pin device with at least one pin which is arranged at or on the first surface.

In the context of the present invention, the term "pin" is to be interpreted widely and extends in particular to profiled elevations of an external contour of this massage pin device. The massage pin device or the pin is also optionally constructed as a substantially non-profiled surface or as a non-elevated surface. Particularly preferably, however, several pins are provided which extend with a cylindrical external contour or a spherical segment-shaped or hemispherical or triangular or pyramidal and/or other geometric external contour from the first surface of the massage pin device.

By virtue of the variable hardness of the massage pins, gentle use is possible even in cases of injury to sensitive areas of the body, without causing further pain.

In the context of the present invention, the surface to be massaged is, in particular, an external surface of the human body, such as the skin of the human body.

A massage characteristic value in the context of the present invention is, in particular, a characteristic value which at least co-determines the transmission of force and/or energy between the first surface and the surface to be massaged, and indeed, in particular, in respect of the surface and/or time distribution of this transmitting force or energy. A massage characteristic value in the context of the present invention is preferably the hardness or the elasticity and/or the geometry of the first surface of the massage device.

BRIEF DESCRIPTION OF THE DRAWINGS

The device according to the invention is illustrated by FIGS. 1 and 2, without limiting it.

DETAILED DESCRIPTION OF THE PREFERRED EMBODIMENTS

Figure 1:
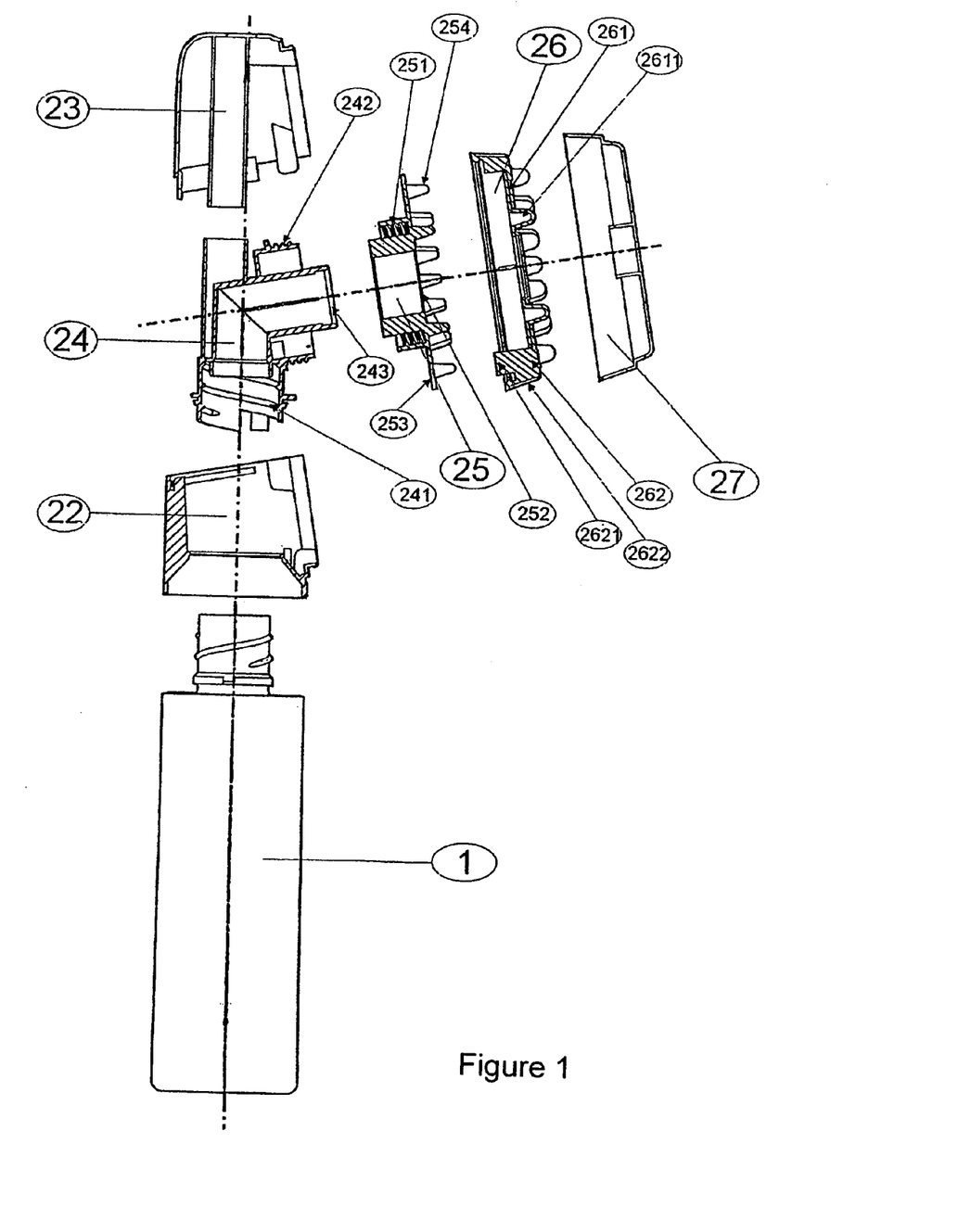
FIG. 1 is an exploded view of an embodiment of the massage appliance according to the invention with individual details, in a side view.

FIG. 1 shows the massage appliance consisting of a container in bottle form (1), the massage device (2) comprising a lower head cap (22), an upper head cap (23), an angle piece (24) with bottle thread (241), a massage thread (242) and valve seat (243), a second element (massage pin inner part) (25) with massage hardness adjustment thread (thread for adjusting the massage characteristic value) (251) and valve section (252), a first element (massage pin outer part) (26) comprising a massage pin disk (261) made of flexible material and a sieve plate with rotary ring (262) made of hard material, and a cover cap (27) in side view.

The bottle (1), which serves as the product container, is closed by a two-part cap (22) and (23), with an angle piece (24) on the inside. The bottle (1), for example produced by the extrusion blow-molding process, is substantially of rectangular construction, it being possible for the edges of the bottle (1) to be rounded.

Figure 2:
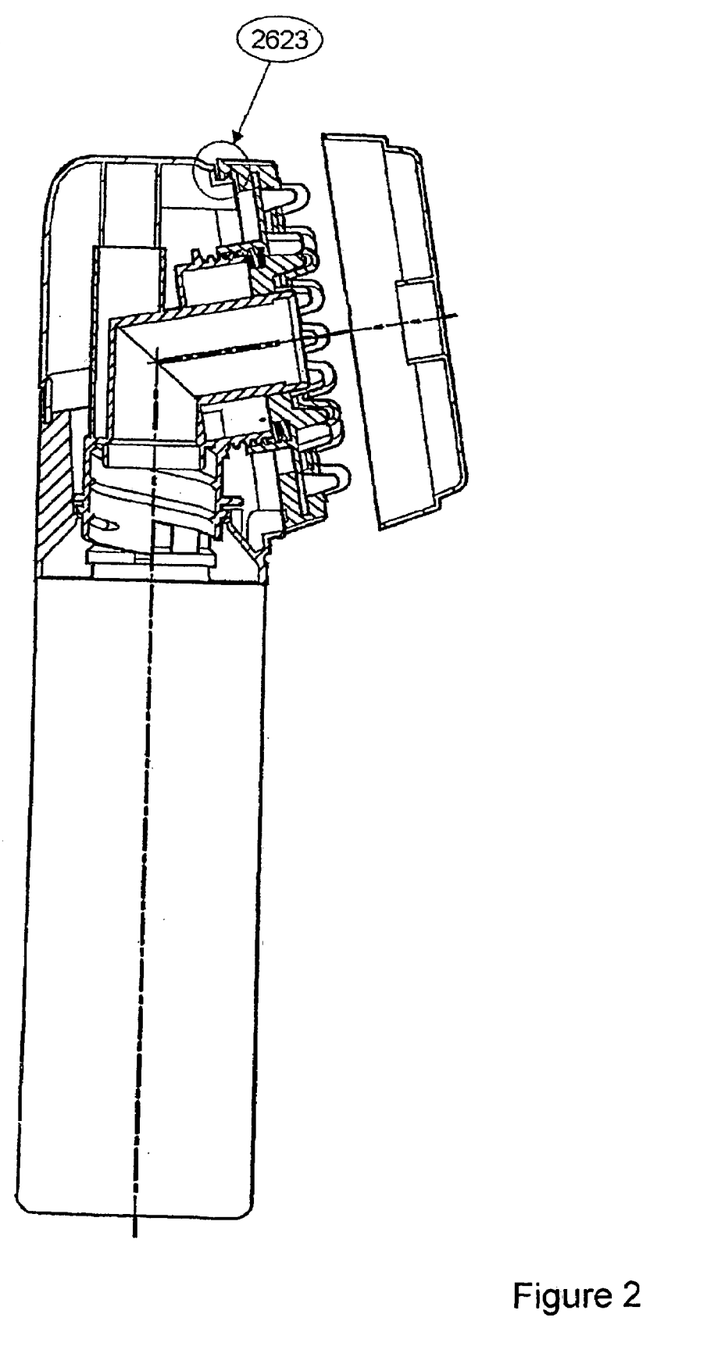
FIG. 2 is an exploded view of an emboidment of the massage appliance according to the invention with individual components assembled, in a side view.

The bottle has, at its end of the bottle neck, a thread which is capable of forming a firm screw connection with the thread (241) of the massage head, of the angle piece (24). The second side of the angle piece likewise has a threaded attachment (242) onto which the adjustable part of the massage device—the second element (massage pin inner part) (25)—is screwed. The first element (massage pin outer part) (26) is pushed onto this arrangement, the carriers (2621) of the massage pin sieve plate (262) snapping into the recesses (253) of the massage pin inner part (25). At the same time, in the area of the rotary ring (2622), a sliding connection is established with the lower and upper head caps in the area (2623) (FIG. 2). Rotation of the ring (2622) leads to a movement of the second element, the massage pin inner part, perpendicular to the direction of rotation and thus to the moving of the rigid pins (254) into and out of the hollow massage pins (2611) of the first element (26), which results in a change in the massage characteristic value and thus in the massage action.

By exerting a gentle pressure on the bottle (1), the user of the massage appliance can press some of the contents through the opening (243), in the area of which a valve can be provided to prevent backward flow, and apply it directly to his skin. With the aid of the massage device, he can now comfortably massage the applied contents into the skin without having to grasp or seek an additional appliance and without coming into contact with the contents.

According to the invention, a defined massage characteristic value can be adjusted steplessly by means of the adjustment device, formed from the first element (26) and second element (25).

The adjustment device has at least one second element which is arranged to be movable relative to the first element (26). In different relative positions of these elements, different massage characteristic values, such as hardness and/or elasticity or geometry, exist in the area of the first surface of the massage device.

Preferably, at least one first element is a pin of substantially hollow construction, and at least one second element is constructed like a mandrel, where this second element extends or can extend into the hollow space of said pin.

In particular, the second element is longer in the direction in which it extends into the pin than it is in the dimensions of the cross-sectional surface arranged perpendicular to this direction. It is furthermore preferable that the second element is shorter in the aforementioned direction than the dimensions of the said cross-sectional surface.

Particularly preferably, the second element can be inserted into the first element or is adjustable in the first element, different massage characteristic values, such as hardness and/or elasticity, existing in the area of the first surface at different depths of insertion or at predetermined different relative positions between the first element and the second element.

The massage pins arranged on the first element can each be of a hollow cylindrical construction and may have, in a first end area, a rounded or semicircle-shaped limit end wall, while in the second end area, lying opposite the first one, there is an opening for receiving a for example piston-shaped mandrel which is axially displaceable inside the pin. The pin is designed with a substantially thin wall and is made of a substantially flexible material. This material has a predetermined elasticity and a predetermined hardness. If the massage device is loaded for massage and a predetermined outer surface area of the pin is in contact with the surface to be massaged, the material in particular and the geometric shape of the pin effect a predetermined elasticity of this pin upon loading of the surface to be massaged and a predetermined hardness. This hardness and elasticity acting in the area of the first surface can be modified by the second element, a piston-shaped inner body, being axially displaced inside the pin, by which means detectable characteristic values such as hardness or elasticity or buckle resistance of the pin are changed in the area of the first surface. For example, the stiffness of the whole arrangement of pins and pistons arranged therein which is measurable in the area of the first surface is changed.

Particular preference is given to a first component, provided with the first surface, which is relatively soft and/or elastic compared to a second component. The second element is arranged to be movable relative to the first element, and, upon a relative movement, the geometry of the first surface or of a surface adjoining this first surface is changed. The material of the first element should be more flexible and/or more elastic than the materials from which the second element is made, so as to bring about a deformation or change in geometry of the first surface.

Preferably, the second element is arranged at least partially in the first element or in a recess of the first element. Particularly preferably, the first element is an exchangeable or adjustable attachment which is fitted or can be fitted onto at least one second element.

According to a particularly preferred embodiment of the invention, at least one first element is of at least partially hollow construction.

Preferably, at least one second element is axially movable inside the first element. This axial mobility is particularly such that the second element is displaceable longitudinally inside the first element.

Particularly preferably, the outer contour of at least one second element is provided with an external thread, and the inner contour of at least one first element is provided with an internal thread, so that the external thread of the second element can engage in the internal thread of the first element.

The first element, preferably in the area of its outer surface, specifically in the area of the first surface of the massage pin device or massage device, is made softer than the second element in a predetermined outer surface area of this second element. This predetermined outer surface area is particularly preferably a surface area which, under predetermined conditions, bears against an inner surface of the first element, specifically at a predetermined relative position between the first element and the second element in an area of the inner surface of the first element which is assigned to what is described as the softer outer surface area of this element.

For example, the second element, comprising a hard pin core, is pushed into the hollow pin of the first element and the latter is thus changed in terms of its hardness, contact surface, mobility, pliability, etc.

At least one first element preferably differs from a second element in terms of its material, the first element particularly preferably being made of a softer material than the second element.

The first element and the second element are in each case made of one or or of different materials.

The first and/or second element is preferably made of plastic, for example polyethylene or polypropylene. The first and/or second element is particularly preferably made of a thermoplastic and/or thermoset and/or elastomer.

The material from which the first element is made preferably has at least one material characteristic value which differs from a material characteristic value of the second element.

Preferably, at least one surface area of the first surface of the massage pin device is substantially rounded.

A preferred massage device according to the invention has a locking device by means of which at least one first element can be held and/or locked in a predetermined relative position with respect to at least one second element.

Particularly preferably, at least one second element can be clamped with respect to at least one first element or within at least one first element in at least one predetermined relative position between these elements.

Particularly preferably, the massage device, in particular the first and/or second components, can be actuated manually. Preferably, the massage device can be actuated mechanically. Particularly preferably, the massage device can be actuated non-electrically.

The massage appliance according to the invention is preferably designed in such a way that the massage device is arranged as a container lid.

Particularly preferably, the invention proposes that the massage device is provided on a container which is constructed as a massage oil bottle or ointment tube, or on another bottle or another container for accommodating fluids or on a container for accommodating solid, pasty or gaseous substances, as are known from the prior art.

The secure connection between massage head and container can also be configured in such a way that the connection can be released for refilling purposes.

A particular advantage of this massage appliance is that cleaning the massage device, in particular the first and second elements and the first surface, is easy because unimpeded passage of water through the guide bodies is ensured by the special construction. As a result, a high preservative concentration in the cleaning composition can be dispensed with. The microbiological safety of the product is also ensured in this manner.

The special construction of the massage device makes pure pressure massage possible, and skin irritations caused by excess friction on the skin surface are thus prevented. In this way, very gentle use of the massage products is ensured. The deeper-lying layers of tissue are exposed to less irritation during massage.

In the context of the invention, a round, angled massage head is preferably used, and the massage is thereby simplified considerably. The massage head is preferably oval and designed in a specific concentric arrangement.

The fact that the massage applicator and container are connected securely to one another, and cannot be separated inadvertently, minimizes the risk of contamination with microbes.

At the same time, a suitable technical design of the bottle and/or of the applicator (e.g. with a valve) ensures that no foreign bodies, for example water or particles of skin, can get into the packaging. Hazardous contamination of the contents is thus prevented. In this way, a high concentration of preservative agents in the content can be dispensed with, which contributes to the compatibility of the product.

Valve systems which are suitable as the valve system according to the invention are those for metered dispensing of a substance from a container, where a discharge opening for dispensing of the substance from the container is provided through at least one of the walls of the container, and a vent is provided through at least one of the walls of the container for the purpose of re-aeration; with a first valve, which seals off the discharge opening for the substance as long as a pressure difference between the inside of the container and the outside of the container is smaller than a first predetermined limit value, and which opens the discharge opening for the substance when the pressure difference between the inside of the container and the outside of the container is greater than the first predetermined limit value, and with a second valve, which opens the vent for re-aeration as long as a pressure difference between the inside of the container and the outside of the container is smaller than a second predetermined limit value, and which seals off the vent for re-aeration when the pressure difference between the inside of the container and the outside of the container is greater than the second predetermined limit value, characterized in that the second valve is made of a flexible material and is designed in the form of a lip which is capable of closing the vent.

According to the invention, the re-aeration opening in the first valve and/or the second valve is integrated in the first valve.

According to the invention, at least one of the valves is made of a flexible material and is designed in the form of a lip which is capable of lying across an opening to seal it off.

The massage products which can preferably be used include medical, dermatological and/or cosmetic preparations which are in the form of gels, emulsions, microemulsions, suspensions, dispersions, colloids, dusting powders, powders and/or pastes and are suitable for percutaneous application.

The combination of the device according to the invention with liquid medical massage compositions which can be used for massaging by means of the special container is particularly advantageous.

Low-viscosity preparations with a viscosity of 0.1 to 10 Pa·s, in particular of less than 10 Pa·s, are particularly advantageous.

According to the invention, these preparations can contain analgesics and antirheumatic agents, in particular nonsteroidal anti-inflammatory agents and salicylic acid derivatives.

Nonsteroidal anti-inflammatory agents according to the invention are arylacetic acid and arylpropionic acid and derivatives thereof (diclofenac, ibuprofen, indomethacin), anthranilic acid derivatives (flufenamic acid, mefenamic acid), pyrazolone derivatives and oxicams.

Salicylic acid derivatives according to the invention are acetylsalicylic acid, methyl salicylate, diethylamine salicylate and hydroxyethyl salicylate.

Active substances according to the invention for widening the vessels and promoting circulation of blood are, inter alia, nicotinic acid and derivatives thereof and capsaicin and derivatives thereof, in particular methyl nicotinate, benzyl nicotinate, N-vanillyl nonanamide, camphor, o-carbamoyl phenoxyacetic acid, extr. fruct. *capsici* (natural capsaicin) and coumarin.

According to the invention, the preparations can also contain heparin and heparinoids as anticoagulants, in particular heparin sodium, mucopolysaccharide polysulfuric acid ester, glucosamine-N-sulfate mucopolysaccharide.

According to the invention, the preparations can also contain essential oils, in particular turpentine oil, rosemary oil, levomenthol, lavender oil, pine needle oil, bergamot oil, mountain pine oil. They can serve as odor-enhancing substances or perfumes and as medically active substances.

According to the invention, skincare agents can be contained in these preparations. Skincare agents include refatting agents, conditioners, peels or active substances.

Auxiliaries according to the invention are triglycerides, glycerol monostearate, partial glycerides from natural plant fatty acids, nonionic emulsifiers, potassium sorbate, cetyl stearyl alcohol, oleyl oleate, decyl oleate, glycerol, polysorbate 60, petroleum jelly, propylene glycol, paraffin, macrogol glycerol triricinoleate 35, macrogol stearate 100, macrogol monolauryl ether, parabens, methylcellulose, sorbitol, isopropyl alcohol, hydroxycellulose, wool wax alcohols, dimethicon, potassium hexadecyl phosphate, cetyl alcohol, stearic acid, cellulose hydroxyethyl ether, butylhydroxytoluene (Oxynex 2004), polyoxypropylene-(15)-stearyl alcohol, polyacrylic acid (Carbopol 940, 934), Ethomeen C25, oleic acid decyl ester, silicon oxide, titanium dioxide, 2,2',2"-nitrilotriethanol, Felicitas PH0/042946, tris[dodecylpoly(oxyethylene)4]phosphate, castor oil, edetic acid, polyoxyethylene-12-cetyl stearyl alcohol, sorbic acid, antioxidants, 2-aminoethanol, spike oil, citric acid, isopropyl myristate, benzyl alcohol, sodium citrate, sodium hydroxide, diisopropylamine, polyol fatty acid ester (Cetiol HE), trometamol, levomenthol.

Using a storage bottle with integrated massage attachment ensures that the product and massage applicator are adapted well to one another and incorrect use by the user is thus ruled out.

Massage applicator and preparation are adapted to one another such that an optimal massage effect is obtained.

The viscosity of the preparation is tailored to this application, and the sliding property of the formulation on the skin is also optimized. In this way, the user achieves an optimal massage effect protective of the skin.

Preservative agents are known to dermatologists for their effect of triggering allergies and damaging skin. By dispensing with the need for preservatives, the compatibility of this product can be considerably improved.

This is important particularly in this type of application, because the product remains for a considerably longer time on the skin. The longer duration of application would otherwise cause irritation by detergent substances.

During application of dermatological preparations, a positive effect can also be obtained for example for tightening of the skin or against cellulite.

The massage formulation is chosen such that there is no problem in cleaning the applicator after use, in particular by rinsing with hot water.

At the same time, the valve in the applicator greatly improves the metering of the preparation during use (massage).

If the applicator is designed in such a way that the massaging intensity can be varied, then it is even possible to massage sensitive parts of the body.

The invention includes a method of warming up before sports activity comprising applying pressure to a massage device comprising: a) a preparation, b) a storage container containing the preparation, and c) a closure for the storage container, said closure comprising a massage device comprising: (i) an outlet opening through which the preparation can be applied to the surface to be massaged, and (ii) an adjustment device comprising: (1) a first element with at least one first surface wherein said first surface contacts the surface to be massaged during a massage, and (2) a second element arranged to be movable relative to the first element, wherein said adjustment device may be used to adjust a massage characteristic value of said first surface, and wherein said massage device is positioned at an angle with respect to the main axis of the storage container.

The following examples, in which preparations for treating local pain and rheumatism are described and for which the device according to the invention can be used to outstanding effect, are intended to explain the compositions according to the invention. The numerical values in the examples denote percentages by weight, based on the total weight of the particular preparation.

EXAMPLES

Massaging and warming ointment for treatment of local pain:

| Benzyl nicotinate | 2.00% by weight |
| Diethylamine salicylate | 5.00% by weight |
| N-Vanillyl nonanamide | 0.30% by weight |

In an aqueous ointment base containing, inter alia, glycerol monostearate, medium-chain triglycerides, partial glycerides, nonionic emulsifiers, potassium sorbate and acidifier.

Massaging and warming gel for treatment of local pain and rheumatism:

| Hydroxyethyl salicylate | 5.00% by weight |
| Benzyl nicotinate | 1.50% by weight |

In an aqueous gel containing, inter alia, isopropyl alcohol, glycerol, polyacrylates (carbomers).

Massaging and warming rub for treatment of local pain and rheumatism:

| Methyl salicylate | 3.00% by weight |
| Benzyl nicotinate | 0.25% by weight |
| Camphor | 2.50% by weight |

In an aqueous gel containing, inter alia, isopropyl alcohol, glycerol, polyacrylates (carbomers), Ethomeen 25.

Massaging and warming oil for treatment of local pain and rheumatism:

| Hydroxyethyl salicylate | 1.80% by weight |
| Benzyl nicotinate | 2.00% by weight |
| Camphor | 3.00% by weight |

In an oil-based formulation containing, inter alia, cetyl stearyl alcohol, sodium cetyl stearyl sulfate, nonionic emulsifiers, paraffin oil, water.

Massaging and warming ointment for local treatment of rheumatism:

| 2-Butoxyethyl nicotinate | 1.10% by weight |
| Sorbic acid | 0.20% by weight |
| N-Vanillyl nonanamide | 0.20% by weight |

In an aqueous ointment base containing, inter alia, cetyl stearyl alcohol, stearic acid, paraffin oil, cetomacrogol, decyl oleate.

That which is claimed:

1. A method of applying, spreading or massaging a preparation on human skin comprising applying pressure to a massage device, comprising:
    a) a preparation,
    b) a storage container containing the preparation, and
    c) a closure for the storage container, said closure comprising a massage device comprising
        (i) an outlet opening through which the preparation can be applied to a surface to be massaged, and
        (ii) an adjustment device comprising:
            (1) a first element with at least one first surface wherein said first surface is structured and arranged to contact the surface to be massaged during a massage, and
            (2) a second element axially movable relative to and within the first element, wherein said adjustment device is structured and arranged to adjust a massage characteristic value of said first surface, and wherein said massage device is positioned at an angle with respect to a main axis of the storage container, the method comprising:

placing said first surface in contact with the surface to be massaged.

2. A method of treating rheumatoid diseases comprising applying pressure to a massage device, comprising:
a) a preparation,
b) a storage container containing the preparation, and
c) a closure for the storage container, said closure comprising a massage device comprising
  (i) an outlet opening through which the preparation can be applied to a surface to be massaged, and
  (ii) an adjustment device comprising
    (1) a first element with at least one first surface wherein said first surface is structured and arranged to contact the surface to be massaged during a massage, and
    (2) a second element axially movable relative to and within the first element,
wherein said adjustment device is structured and arranged to adjust a massage characteristic value of said first surface, and
wherein said massage device is positioned at an angle with respect to a main axis of the storage container, the method comprising:
placing said first surface in contact with the surface to be massaged.

3. A method of warming up before sports activity comprising applying pressure to a massage device comprising:
a) a preparation,
b) a storage container containing the preparation, and
c) a closure for the storage container, said closure comprising a massage device comprising
  (i) an outlet opening through which the preparation can be applied to a surface to be massaged, and
  (ii) an adjustment device comprising:
    (1) a first element with at least one first surface wherein said first surface is structured and arranged to contact the surface to be massaged during a massage, and
    (2) a second element axially movable relative to and within the first element,
wherein said adjustment device is structured and arranged to adjust a massage characteristic value of said first surface, and
wherein said massage device is positioned at an angle with respect to a main axis of the storage container, the method comprising:
placing said first surface in contact with the surface to be massaged.

4. A massage appliance, comprising
a) a storage container; and
b) a closure for the storage container, said closure comprising a massage device comprising
  (i) an outlet opening, and
  (ii) an adjustment device comprising
    (1) a first element with at least one first surface wherein said first surface is structured and arranged to contact a surface to be massaged during a massage, and
    (2) a second element axially movable relative to and within the first element,
wherein said adjustment device is structured and arranged to adjust a massage characteristic value of said first surface, and
wherein said massage device is positioned at an angle with respect to a main axis of said storage container.

5. The massage appliance as claimed in claim 4,
wherein said first element comprises skin contacting members, said skin contacting members being at least one of:
hollow members; and
substantially flexible material members; and
wherein said second element comprises rigid members which move with the skin contacting members.

6. A massage appliance, comprising:
a) a preparation,
b) a storage container containing the preparation, and
c) a closure for the storage container, said closure comprising a massage device comprising
  (i) an outlet opening through which the preparation can be applied to a surface to be massaged, and
  (ii) an adjustment device comprising:
    (1) a first element with at least one first surface wherein said first surface is structured and arranged to contact the surface to be massaged during a massage, and
    (2) a second element axially movable relative to and within the first element,
wherein said adjustment device is structured and arranged to adjust a massage characteristic value of said first surface, and
wherein said massage device is positioned at an angle with respect to a main axis of the storage container.

7. The massage appliance as claimed in claim 6, wherein the massage characteristic value can be steplessly adjusted.

8. The massage appliance as claimed in claim 7, wherein the massage characteristic value can be adjusted by rotation of said second element, horizontal displacement of said second element, vertical displacement of said second element, or any combination thereof.

9. The massage appliance as claimed in claim 8, wherein the massage characteristic value can be adjusted by rotation of said second element.

10. The massage appliance as claimed in claim 8, wherein the massage characteristic value can be adjusted by horizontal displacement of said second element.

11. The massage appliance as claimed in claim 8, wherein the massage characteristic value can be adjusted by vertical displacement of said second element.

12. The massage appliance as claimed in claim 6, wherein the massage characteristic value represents the hardness of the first surface.

13. The massage appliance as claimed in claim 6, wherein the massage characteristic value represents the elasticity of the first surface.

14. The massage appliance as claimed in claim 6, wherein the massage characteristic value represents the surface geometry of the first surface.

15. The massage appliance as claimed in claim 6, wherein the first element, the second element, or both the first element and the second element are either partially or completely made of plastic.

16. The massage appliance as claimed in claim 15, wherein said plastic includes at least one plastic selected from the group consisting of polyethylene and polypropylene.

17. The massage appliance as claimed claim 6, wherein said first surface comprises one or more massage pins.

18. The massage appliance as claimed in claim 17, wherein at least one of said one or more massage pins is rounded.

19. The massage appliance as claimed in claim 17, wherein said one or more massage pins are arranged in a geometric pattern.

20. The massage appliance as claimed in claim 17, wherein said one or more massage pins are arranged concentrically.

21. The massage appliance as claimed in claim 6, wherein said massage device is configured to be transferable to a different storage container.

22. The massage appliance as claimed in claim 6, wherein said preparation can be conveyed from said storage container to said outlet opening (i) via an ascending tube.

23. The massage appliance as claimed in claim 6, wherein said preparation has a viscosity of from 0.1 to 10 Pa·s.

24. The massage appliance as claimed in claim 6, wherein said preparation is selected from the group consisting of gels, emulsions, oils, microemulsions, suspensions, dispersions, colloids, dusting powders, powders, and pastes.

25. The massage appliance as claimed in claim 6, further comprising a valve separating said storage container from said massage device.

26. The massage appliance as claimed in claim 6, wherein said preparation is capable of producing a wanning effect when massaged onto human skin.

27. The massage appliance as claimed in claim 6, wherein said preparation is capable of stimulating blood circulation when massaged onto human skin.

28. The massage appliance as claimed in claim 6, wherein said preparation has a pain-relieving effect when massaged into the human skin.

29. The massage appliance as claimed in claim 6, wherein said preparation comprises at least one compound selected from the group consisting of analgesic substances, nonsteroidal anti-inflammatory substances, salicylic acid derivatives, arylacetic acid, arylpropionic acid and derivatives thereof, anthranilic acid derivatives, pyrazolone derivatives, oxicams, acetylsalicylic acid, methyl salicylate, diethylamine salicylate, and hydroxyethyl salicylate.

30. The massage appliance as claimed in claim 6, wherein said preparation comprises at least one compound selected from the group consisting of active substances for widening the vessels or stimulating blood flow, nicotinic acid and derivatives thereof, capsaicin and derivatives thereof, methyl nicotinate, benzyl nicotinate, N-vanillyl nonanamide, camphor, o-carbomyl phenoxyacetic acid, extr. fruct. Capsici, and coumarin.

31. The massage appliance as claimed in claim 6, wherein said preparation comprises at least one compound selected from the group consisting of anticoagulants, heparin, heparinoids, heparin sodium, mucopolysaccharide polysulfric acid ester, and glucosamine-N-sulfate mucopolysaccharide.

32. The massage appliance as claimed in claim 6, wherein said first element is made of a softer material than said second element.

33. The massage appliance as claimed in claim 6,
wherein said first element comprises skin contacting members, said skin contacting members being at least one of:
hollow members; and
substantially flexible material members; and
wherein said second element comprises rigid members which move with the skin contacting members.

* * * * *